US010464033B2

(12) United States Patent
Seiler et al.

(10) Patent No.: US 10,464,033 B2
(45) Date of Patent: Nov. 5, 2019

(54) APPARATUS FOR TREATING AND COOLING FOUNDRY MOULDING SAND

(71) Applicant: Maschinenfabrik Gustav Eirich GmbH & Co. KG, Hardheim (DE)

(72) Inventors: Andreas Seiler, Tauberbischofsheim (DE); Feng Li, Jiangyin (CH); Stefan Gerl, Werbach (DE); Paul Eirich, Hardheim (DE)

(73) Assignee: Maschinenfabrik Gustav Eirich GmbH & Co. KG, Hardheim (DE)

( * ) Notice: Subject to any disclaimer, the term of this patent is extended or adjusted under 35 U.S.C. 154(b) by 128 days.

(21) Appl. No.: 15/509,807

(22) PCT Filed: Nov. 20, 2015

(86) PCT No.: PCT/EP2015/077278
§ 371 (c)(1),
(2) Date: Mar. 8, 2017

(87) PCT Pub. No.: WO2016/083270
PCT Pub. Date: Jun. 2, 2016

(65) Prior Publication Data

US 2018/0229196 A1 Aug. 16, 2018

(30) Foreign Application Priority Data

Nov. 28, 2014 (DE) ........................ 10 2014 117 509

(51) Int. Cl.
*F26B 7/00* (2006.01)
*B01F 15/06* (2006.01)
(Continued)

(52) U.S. Cl.
CPC .............. *B01F 15/063* (2013.01); *B01F 3/18* (2013.01); *B01F 7/007* (2013.01);
(Continued)

(58) Field of Classification Search
CPC ..... B22C 5/044; B22C 5/08; B01F 15/00876; B01F 7/18; B01F 7/162; B01F 2015/061
(Continued)

(56) References Cited

U.S. PATENT DOCUMENTS 3,050,795 A 8/1962 Dietert
3,406,950 A 10/1968 McIlvaine
(Continued)

FOREIGN PATENT DOCUMENTS

CN 203507857 U 4/2014
DE 1558105 A1 3/1970
(Continued)

OTHER PUBLICATIONS

Office Action Re Chinese Patent Application CN201580064627.6, dated Jun. 27, 2018 (and English Translation).
(Continued)

*Primary Examiner* — John P McCormack
(74) *Attorney, Agent, or Firm* — Paul & Paul

(57) ABSTRACT

The present invention concerns an apparatus for treating and cooling foundry molding sand, comprising a mixing container and a mixing tool rotatable about a drive shaft, wherein there is provided an air feed for the feed of air into the container interior. To provide an improved apparatus with which a more uniform fluidized layer is produced as far as possible over the entire cross-section of the mixing container, wherein moreover the proportion of the solid particles entrained with the gas flow is to be reduced, it is proposed according to the invention that the mixing tool has at least two mixing vanes spaced from each other in the vertical direction and at least one mixing vane has a mixer blade with a surface which is inclined relative to the horizontal.

19 Claims, 4 Drawing Sheets

(51) Int. Cl.

| | |
|---|---|
| ***B01F 7/00*** | (2006.01) |
| ***B01F 7/16*** | (2006.01) |
| ***B01F 7/18*** | (2006.01) |
| ***B01F 15/00*** | (2006.01) |
| ***B22C 5/04*** | (2006.01) |
| ***B22C 5/08*** | (2006.01) |
| ***B01F 3/18*** | (2006.01) |
| *B01F 3/00* | (2006.01) |

(52) U.S. Cl.
CPC ...... *B01F 7/00633* (2013.01); *B01F 7/00641* (2013.01); *B01F 7/00975* (2013.01); *B01F 7/162* (2013.01); *B01F 7/18* (2013.01); *B01F 15/00876* (2013.01); *B22C 5/044* (2013.01); *B22C 5/08* (2013.01); *B01F 2003/0007* (2013.01); *B01F 2015/061* (2013.01)

(58) Field of Classification Search
USPC ... 34/391, 62, 392, 393, 394, 395, 254, 304, 34/378, 428; 366/301, 300, 297, 296, 3, 366/4, 66, 101, 102, 104, 107, 257, 258, 366/279, 282, 292, 295
See application file for complete search history.

(56) References Cited

U.S. PATENT DOCUMENTS

| | | | | |
|---|---|---|---|---|
| 3,456,906 | A * | 7/1969 | Troy | B01F 7/165 241/102 |
| 3,572,653 | A | 3/1971 | Boenisch | |
| 3,722,831 | A * | 3/1973 | Bialas | B01F 7/1625 366/291 |
| 3,934,858 | A | 1/1976 | Parsonage et al. | |
| 5,382,002 | A * | 1/1995 | Evans | B09C 1/06 266/173 |
| 5,788,621 | A * | 8/1998 | Eady | B04B 1/02 494/2 |
| 5,934,803 | A * | 8/1999 | Hutter | A61B 17/8827 366/139 |
| 2010/0149903 | A1* | 6/2010 | Imai | B01F 3/1221 366/77 |

FOREIGN PATENT DOCUMENTS

| | | | |
|---|---|---|---|
| DE | 2952403 | A1 | 7/1981 |
| DE | 69412115 | T2 | 3/1999 |
| DE | 9925720 | C1 | 11/2000 |
| DE | 202007005577 | U1 | 6/2007 |
| EP | 2716384 | A1 | 4/2014 |
| GB | 2066683 | A | 7/1981 |
| JP | S51-22218 | B | 7/1976 |
| JP | H10-277698 | | 10/1998 |
| JP | 2000-176271 | A | 6/2000 |
| JP | 2002-102668 | A | 4/2002 |
| TW | M375563 | U | 3/2010 |
| WO | 2007/013415 | A1 | 2/2007 |

OTHER PUBLICATIONS

Office Action, dated Aug. 27, 2018, Taiwan Patent Application TW104133703.

Nora Linder, The International Bureau of the World Intellectual Property Organization, Translation of the International Preliminary Examination Report on Patentability, PCT/EP2015/077278, dated Jun. 8, 2017.

Office Action, Japanese Patent Appl. 2017-518509, dated May 28, 2018 (and English Translation).

* cited by examiner

APPARATUS FOR TREATING AND COOLING FOUNDRY MOULDING SAND

CROSS-REFERENCE TO RELATED APPLICATIONS

This application is a 371 national stage application of International Application PCT/EP2015/077278, filed Nov. 20, 2015, and claims the priority of German Application No. 10 2014 117 509.3, filed on Nov. 28, 2014.

The present invention concerns an apparatus for cooling warm loose bulk particle materials, in particular foundry moulding sand.

Used foundry moulding sand can be re-used if the foundry moulding sand is treated. For that purpose it is necessary to cool down the used sand.

Such an apparatus is known for example from DE 1 508 698. The apparatus described therein comprises a mixing container and two vertically arranged drive shafts for a mixing tool. The foundry moulding sand to be cooled is introduced into the mixing container on one side and removed on the other side. While the foundry sand to be cooled is passing through the apparatus the foundry sand is thoroughly mixed by means of the mixing tools. In addition the mixing container has an opening for the feed of air in the container wall directly at the container bottom.

That apparatus seeks to produce a fluidised layer through which air passes and which is sprayed with water and which is mechanically supported in order to cool down the foundry sand heated to up to 150° C. by the preceding casting operation to the temperature of use of about 45° C. by evaporative cooling.

The mixing container is integrated into a machine frame. The mixing container itself has two polygonal portions which pass through each other. Arranged at the centre of each of the two portions is a corresponding rotatable mixing tool. The mixing vanes fitted to the shaft typically have plate-shaped paddles which are moved on vertically arranged holders of radially extending rotating carrier arms. The plate-shaped paddles produce an effect only on a circular ring path which is delimited substantially locally around the paddles, of small extent. In the apparatus described in DE 1 508 698 the two portions pass through each other so that, upon actuation of the two mixing tools, it is necessary to ensure that they do not collide with each other, and that necessitates a specifically adapted motion control system.

Particularly when very large amounts of foundry moulding sand are to be cooled down with the apparatus and therefore the container diameter is of a correspondingly large dimension the known apparatuses only succeed in implementing irregular cooling, which markedly restricts the quality of the foundry moulding sand which is to be further used. An improved moulding sand quality can be achieved for example by the use of vacuum mixers which however are relatively costly.

In the case of the inexpensive apparatuses as are shown in DE 1 508 698 the cooling air which is introduced at the edge blasts free the flow passages through the sand bed only in the immediate area around the inlet openings and escapes upwardly over a relatively short path without performing the actual function of uniform fluidisation of the bulk material and cooling with a high level of efficiency. The centre of the material to be mixed, in the container centre, is not reached at all by the air as that material comes into contact with the air as it flows out and up only on an outer annular path in the immediate proximity of the air inlet openings. By virtue of the substantially higher flow resistance of the loose material in the radial direction towards the mixing tool shaft the air flows vertically upwardly after issuing from the slot-shaped opening and following the very slight pressure drop. At the centre of the mixing container the sand is only slightly mixed by the rotating vanes by virtue of the low peripheral speed prevailing there and the low speed differences and is urged slowly radially outwardly by the outwardly facing vane inclination in order to convey the sand into the cooling zone.

As a consequence of the speed differences the residence time of the material to be mixed also involves large differences between the material in the centre of the container and at the outer periphery. In the worst-scenario case the material to be mixed passes through the cooler from the feed opening disposed on the central axis to the oppositely disposed discharge opening in the region of the drive shafts without substantial contact with the supplied cooling air. In addition very high exit speeds from the bed of material to be mixed are observed due to the locally occurring vertical flow passages in the wall region, and those exit speeds entrain a large amount of solid particles by virtue of the high speed and fluctuations in the flow.

Therefore DE 199 25 720 already describes withdrawing the cooling air by a suction removal fan by way of a generally centrally arranged opening in the housing cover and cleaning it in a gas cyclone which is connected downstream of the cooler and which is generally of very large volume. In that case the sand and additive components which are entrained in the gas flow are very substantially separated off in the cyclone and added to the sand discharged from the cooler. By virtue of the mode of operation of a gas cyclone the large heavy sand particles are preferably separated off there while the fine components which are in a state of suspension like bentonite and carbon follow the gas flow and are completely discharged. Complete separation of the particles from the gas flow does not occur. By virtue of the undefined composition of the fine components which are later separated off in a filter those components have to be disposed of and compensated for by the addition of fresh additives. The sand which is withdrawn from the bottom discharge of the cyclone and which is generally rather too dry is put on to the cooled sand on a conveyor belt. Mixing of those discharged sand particles with the moistened sand no longer takes place, which can lead to problems in the moulding machines if further sand homogenisation and moistening is no longer implemented at a downstream location.

Taking the described state of the art as the basic starting point therefore the object of the present invention is to provide an improved apparatus with which a more uniform fluidised layer is achieved as far as possible over the entire cross-section of the mixing container, while in addition the proportion of solid particles entrained with the gas flow is to be reduced.

According to the invention that is achieved by an apparatus for treating and cooling foundry moulding sand, comprising a mixing container and a mixing tool rotatable about a drive shaft, wherein there is provided an air feed for the feed of air into the container interior. According to the invention the mixing tool has at least two mixing vanes spaced from each other in the vertical direction and at least one mixing vane has a mixer blade which is inclined relative to the horizontal and which is preferably inclined downwardly in the direction of rotation of the mixing tool. In that case the direction of rotation is predetermined by the drive device of the mixing tool. Therefore the drive device of the mixing tool is so designed that it drives the mixing tool in such a way that the mixing tools are inclined downwardly in the direction of rotation. In an alternative embodiment the drive device can also be so designed that if required the direction of rotation of the mixing tool can be altered.

The use of mixing vanes which are displaced relative to each other in the vertical direction leads to better thorough mixing of the material to be mixed. In that case preferably the mixing vanes extend in a horizontal direction from the drive shaft. The inclination of the mixer blade is such that the mixer blade which is inclined downwardly in the direction of rotation of the mixing tool provides that the material to be mixed is lifted in the mixing process, whereby there is formed directly behind the mixer blade within the material being mixed a cavity in which the supplied air can be distributed over the entire width and length of the mixer blade in the material being mixed. Therefore the mixer blade preferably extends over at least half the radius of the circle described by the outer portion of the mixer blade as it rotates. In an embodiment it is provided that the mixer blade extends from the container wall to the drive shaft.

To further improve mixing of the cooling air with the material to be mixed in a preferred embodiment the mixer blade extends substantially to the container wall. In that case the spacing between the mixer blade and the container wall is preferably less than 100 mm and is best between 20 and 60 mm. That measure provides for layer-wise loosening along the tool profile in the sand bed. It is also possible for a preferably flexible attachment to be fixed to the mixer blade, which attachment projects radially beyond the mixer blade in the direction of the container wall and contacts same so that in operation the attachment rubs over the container wall.

In fluidic respects the mixer blade is so designed that the material to be mixed is lifted upwardly so that formed on the side of the mixer blade, that faces away from the flow, is a cavity which serves as a flow passage for incoming air. In the ideal situation the air can flow only by way of the cavity between the drive shaft and the container wall and, on the side remote from the solids flow, can rise through the material being mixed, which drops downwardly behind the mixing tool again due to the force of gravity so that the upwardly flowing air is caused to flow uniformly through the material being mixed as far the container centre. That configuration provides that, with a sufficiently high peripheral speed for the tools, a local upward flow of the air is prevented substantially only in the region of the air outlet openings. Tests have shown that the drive for rotating the mixing tool is preferably so designed that the mixer blade has a peripheral speed at its radially outer end of between 2 and 75 m per second and preferably between 30 and 60 m per second.

A preferred embodiment provides that the container wall is inclined so that the container cross-section becomes larger in an upward direction from the container bottom. In that case preferably each mixing vane has a mixer blade, wherein the spacing between mixer blade and container wall is approximately the same for both mixer blades. By virtue of the inclined container wall and the arrangement of the two mixer blades at different heights, the consequence of this is that the further upwardly arranged mixer blade has to extend radially further outwardly.

In a further preferred embodiment at least one mixer blade of each mixing tool is arranged substantially at the container bottom.

By virtue of a suitable number and arrangement of mixer blades in mutually superposed relationship in conjunction with the choice of a suitable mixing tool peripheral speed it is possible to achieve mechanical support for the fluidised bed such a way that the air flows through the sand bed, distributed substantially homogeneously over the entire cross-section, and the sand is uniformly cooled.

The good and uniform distribution of the air over the entire cross-section of the sand bed also provides that the flow speeds at the surface of the loose bulk material is reduced so that the discharge of particles with the air flow is markedly reduced.

In a preferred embodiment the mixing container has at least two mixing portions, wherein provided in each mixing portion is a respective mixing tool rotatable about a drive shaft, wherein preferably each mixing tool has at least two mixing vanes spaced from each other in the vertical direction.

In that case the peripheral speed of the mixing vanes and the direction of rotation can be different in the individual mixing portions.

In this embodiment the inlet for the foundry moulding sand to be cooled down is in the one portion while the corresponding outlet is in the other portion so that the foundry moulding sand has to pass successively through both mixing portions. In a preferred embodiment each mixing tool has a mixer blade arranged substantially at the container bottom, wherein the two mixing tools are spaced from each other so far that the two mixer blades arranged at the container bottom do not touch each other in any position of the mixing tools. The circular paths of the two mixer blades arranged at the container bottom therefore tangentially adjoin each other in the closest case.

The vertically higher mixer blades of different mixing tools are preferably arranged at different axial heights. In that case they are so designed that their circular paths overlap. The differing arrangement in a vertical direction ensures that a collision cannot occur. A configuration close to the wall in respect of all tools is possible by the described structure. In addition both mixing tools can be driven independently of each other at different rotary speeds without a collision having to be feared. In that way it is possible to attribute to the mixing tools in the individual mixing container portions, a rotary speed which is optimum for the respectively predominant task in terms of process engineering. Thus the tool speed of the mixing chamber portion at the material inlet side can be optimised for efficient mixing in of the water while the rotary speed of the tool in the following mixing chamber portion can be adapted to the optimum through flow of cooling air through the sand bed with at the same time a reduced particle discharge as here the stickiness of the particles has already decreased due to the reduction in moisture. The mixing tool geometry in the different planes and mixing chamber portions can also be different so that this provides for corresponding optimisation in regard to the flow through the sand bed with at the same time a minimised discharge of solids from the bed.

By way of example the air feed can have openings in the container wall, through which air can be blown into the container interior. In that case the openings are preferably arranged at the same vertical height as the mixer blade which extends substantially to the container wall.

An alternative embodiment provides that the air feed is passed by way of the mixing tool itself, which for example has a hollow shaft. By way of example the mixer blade can have corresponding air outlet openings on its side oriented in opposite relationship to the direction of rotation. It is self-evident that a combined air inlet would also be possible, by way of openings in the container wall and by way of openings in the mixing tool.

By virtue of the structure involved the peripheral speed of the mixer blade increases with increasing spacing from the drive shaft, with the consequence that the mixing action increases in the direction of the container wall. With the cross-section of the mixer blade remaining the same therefore, the mixing intensity will also increase with an increasing operative diameter as the peripheral speed becomes higher with an increasing radius. It is possible to counteract that physical law by a suitable configuration for the cross-sectional shape of the blades from the inside outwardly. For example the mixer blade can be of a width which increases in the radial direction. Alternatively or in combination therewith the angle of inclination of the mixer blade relative to the horizontal can decrease in the radial direction.

The mixer blade can be flat or curved. The angle of inclination relative to the horizontal is preferably between 15° and 60°, and particularly preferably between 20° and 50°.

In a further preferred embodiment the mixer blade is in the form of an angled profile, wherein the inner angle is opposite to the direction of rotation of the mixer blade and is preferably between 90° and 180°. By virtue of that measure it is possible to provide a larger cavity which faces away from the solids flow so that the air which flows into the passage formed in that way from the inside or the outside can penetrate to the end of the air passage formed, with at the same time a reduced pressure drop.

Alternatively the mixer blade can also be a substantially closed polygonal profile like for example a rectangular or triangular profile, wherein suitable air outlet openings are disposed on the side facing away from the flow so that the cooling air can be introduced into the material to be mixed by way of the profile.

In a further embodiment fixed on radially inner portions of the mixer blade for compensating for the lower peripheral speed are ploughshare-like attachments which act at one or both sides in order on the one hand to reinforce the lifting action of the mixture and the flow thereof over the blades and on the other hand to achieve an improved mixing action. In combination with air outlet openings arranged beneath the ploughshares it is therefore possible to provide a falling curtain of sand which, by virtue of its larger heat-exchange and substance-exchange surface area, achieves a higher level of cooling efficiency upon contact with the discharging air.

Particularly in the case of fine sand qualities it may be advantageous if the mixer blade of the uppermost mixing vane is inclined in opposite relationship so that the material to be mixed is guided downwardly in order to counteract an excessive turbulence effect and related thereto an excessive discharge from the cooling device with the discharge gas flow.

The spacing between the air inlet openings arranged in the mixing container and the radially outer end of the mixer blade should be as small as possible in order to ensure that an excessively large proportion of the cooling air does not already escape upwardly before reaching the mixer blade.

Tests have shown that the average flow speed of the cooling air in the outlet region of the air inlet openings should be between 15 and 35 m/s and particularly preferably between 20 and 30 m/s. Even if basically the angle of inclination of the container wall can assume any desired value between 0 and 45° the inclination is preferably between 15 and 35° and particularly preferably between 20 and 30° relative to the vertical.

In a further embodiment disposed at the radially outer ends of the mixer blades are fixed, or alternatively also spring-loaded, extension portions which are moveable in a radial direction and comprising for example plastic, which rubbingly touch the container wall and thus make direct contact between the air outlet opening and the side of the mixing vane, that faces away from the solids flow.

In a further preferred embodiment even more than two, namely three or even more, mixing chamber portions are arranged one after the other, through which the material to be mixed successively flows. In such a configuration the water is substantially mixed in and homogeneously distributed in the first chamber at the inlet side, while it is only in the second chamber that intensive aeration of the sand bed and thereby evaporative cooling is achieved. In the third and each further following chamber the quality of the cooled sand can be subsequently corrected by the addition of for example water or other additives. For example the foundry moulding sand should then have a residual moisture content of between 3.0 and 3.5% upon leaving the apparatus in order to re-activate the bentonite which encases the sand and which provides the shaping properties of the moulding sand and to permit direct use in the moulding machine. In that case it may be advantageous if the mixing tool in the third mixing chamber portion, that is to say the portion through which the material to be mixed last flows, has mixer blades which are inclined upwardly in the direction of rotation, thereby ensuring that a shearing loading on the material being mixed occurs in the last mixing chamber portion. In general it is also not necessary in the last mixing chamber portion for air to be supplied thereto so that it is possible to dispense with corresponding openings in that portion. For many situations of use it may also be advantageous if the mixing chamber tool in the third mixing chamber portion is driven in a direction of rotation in opposite relationship to the mixing chamber tool in the second mixing chamber portion.

As already mentioned the local through-flow speed is markedly reduced by the measures according to the invention, with the consequence that fewer solid particles are entrained and discharged by the air flow.

Nonetheless in a particularly preferred embodiment it may be advantageous if the rising gas flow is liberated as extensively as possible from the entrained solid particles, while still in the housing. Therefore a preferred embodiment provides that a solids separator is arranged above the mixing tool. In a preferred embodiment separation of the solid particles is effected in a turbulent fluidised flow, for example in a rotational flow generated by a rotor. The forced rotational flow in that case produces a corresponding centrifugal field which can be adjusted in terms of its strength by the choice of the speed of rotation of the rotor. There is therefore the possibility of adjusting the separation effectiveness and the separation grain size. Accordingly for example if the rotary speed is sufficiently increased even the particularly fine additive components contained in the gas flow can be almost completely recycled.

The solution according to the invention provides for a very compact structural configuration for the cooler, while at the same time almost all solid particles are retained in the mixer.

Further advantages, features and possible uses of the present invention will be apparent from the description hereinafter of preferred embodiments of the invention. In the drawing:

FIG. 1 shows a sectional view of a first embodiment according to the invention of a cooling apparatus, FIG. 2 shows a sectional view of a second embodiment according to the invention, FIG. 3 shows a detail view of a mixer with a plurality of different mixer blades, and FIGS. 4 to 8 show cross-sectional views of different mixer blades.

FIG. 1 shows a sectional view of a first apparatus according to the invention. The apparatus 1 for treating and cooling foundry moulding sand has a mixing container 2 arranged in a housing 3. The mixing container 2 has two mixing portions, in the centre of which is arranged a respective drive shaft 4. The drive shafts 4 in turn each have a plurality of mixing vanes 30 (best seen in FIG. 3) with corresponding mixer blades. The apparatus 1 has an inlet 5 and an outlet 5', by way of which hot foundry moulding sand can be introduced into the mixing container 2 for example by means of a conveyor belt 6 and the treated sand can be discharged from the mixing container 2 again. Provided in the inclined container wall 2 are a series of cooling air openings 7 by way of which cooling air can be introduced into the mixing container 2. Near the bottom the two drive shafts 4 respectively have mixing vanes 30 which extend in opposite directions and to which a respective mixer blade 8 is mounted. The two drive shafts 4 are arranged spaced from each other in such a way that the mixer blades 8 which are arranged near the bottom cannot collide with each other in any rotational position. Arranged spaced in a vertical direction relative to the mixing vanes 30 near the bottom are further pairs of mixing vanes 30 which are also equipped with respective corresponding mixer blades. In the illustrated embodiment all mixer blades are inclined downwardly so that, when the drive shaft is rotated in the intended direction, the foundry moulding sand in the mixing container 2 is lifted and flows over the inclined mixer blade surface. The mixer blades of the second and third planes are arranged at a height corresponding to the vertical height of the air inlet openings 7 in the container wall 2. In addition the mixer blades in the planes 2 and 3 are so arranged that they extend almost to the air inlet openings 7. The two drive shafts 4 are driven by means of the drive motors 9. Arranged in the cover of the housing 3 is a solids separator 11 comprising a wheel which is provided with fins and which can be rotated by means of the drive motor 10. The cooling air which is supplied by way of the air inlet openings 7 is then sucked away by way of the intermediate spaces between the fins of the solids separator 11. The driven wheel of the solids separator 11 generates a turbulent flow in which the solid body components contained in the air to be sucked away are deposited and drop back into the mixing container.

FIG. 2 shows a diagrammatic sectional view of an alternative embodiment of the invention. In this case the same references are used to denote the same components. In the FIG. 2 embodiment the feed of cooling air is effected on the one hand by way of a drive shaft 4 which is in the form of a hollow shaft and in which air flows by means of the feed 12 into the passage 15 and by way of the passage into corresponding openings within the mixer blades 8, 8', 8" and 8'", into the material to be mixed. In addition or alternatively thereto air can be introduced into the housing by way of the air feed 13 and into the material to be mixed by way of the air inlet openings 7. It will be clearly seen in this embodiment that the mixer blades of the upper planes are of a longer radial extent than the mixer blades in the lower plane.

The mixer blades 8, 8', 8" and 8'" extend substantially to the container wall. To avoid damage to the mixer blades however a small gap must remain. By way of example therefore the drawing shows in relation to a mixer blade that the mixer blades can have an extension portion 14 of plastic, which can also be pressed by means of springs against the container wall in order to reduce the proportion of the cooling air feed, which flows directly vertically upwardly.

FIG. 3 shows by way of example different embodiments of mixer blades. In principle, as shown in the embodiment denoted by reference 17, the mixer blade can extend uniformly from the drive shaft to the container wall. It will be appreciated however that curved shapes would also be possible, as in the case of the embodiment denoted by reference 15, or shapes which are enlarged fan-like, as with the embodiment denoted by reference 16.

In the embodiment denoted by reference 18 ploughshare-like attachments 19 are provided on the mixing vanes.

FIG. 4 shows a cross-sectional view through a mixer blade 20 which here comprises a single inclined surface. Upon movement of the mixer blade 20, there is formed behind the mixer blade a zone which is kept substantially free of material to be mixed and into which the cooling air introduced into the mixing container through the air feed openings 7 can flow radially inwardly along the mixer blades. In that case the contour of the air outlet opening 7 is ideally so selected that, in combination with the geometry of the mixer blade, it is possible to provide for an intake flow of air which is as uniform and as long-lasting as possible, into the zone which is kept free of material to be mixed, behind the mixer blade.

Figure 1:
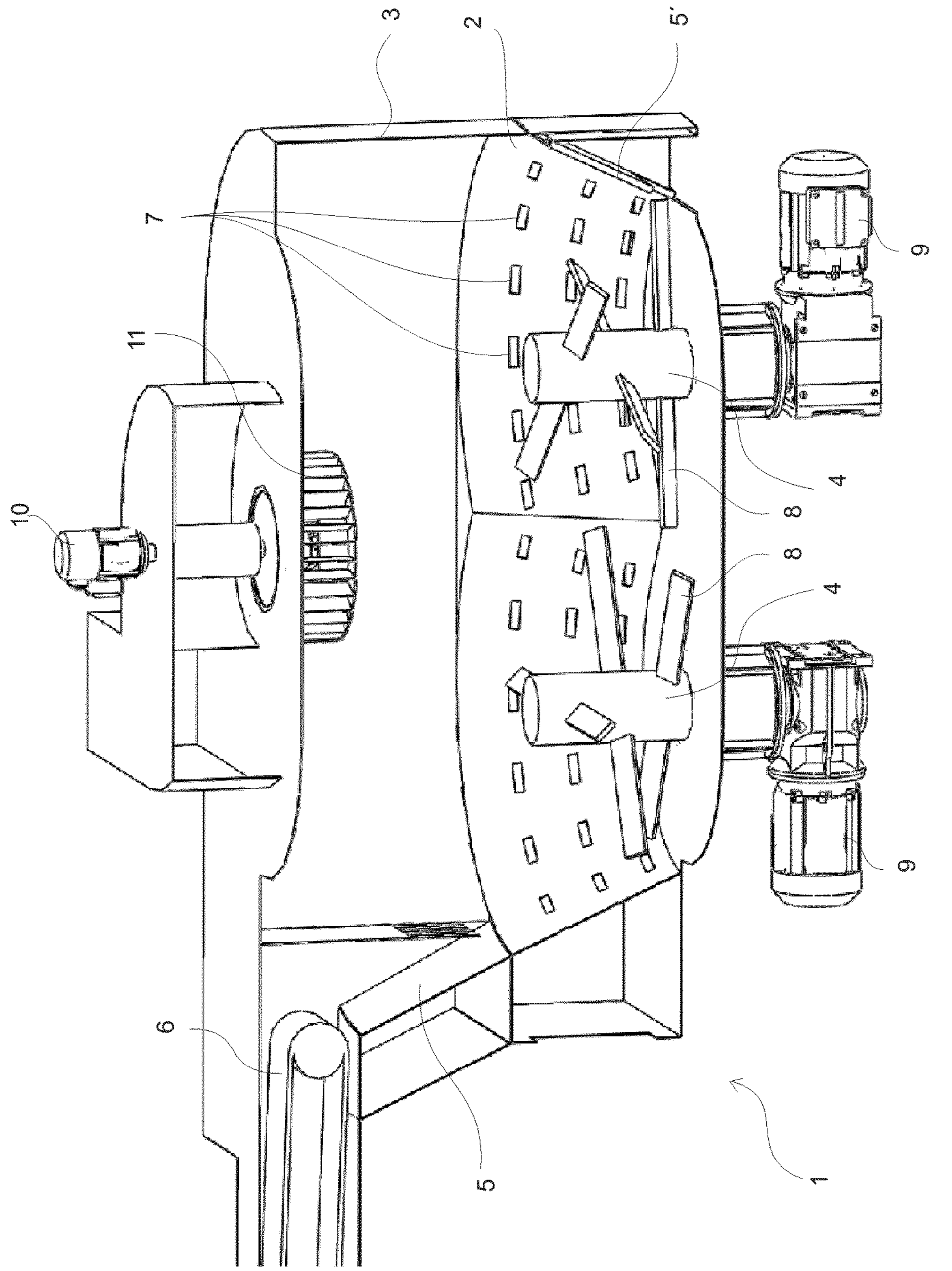
Figure 2:
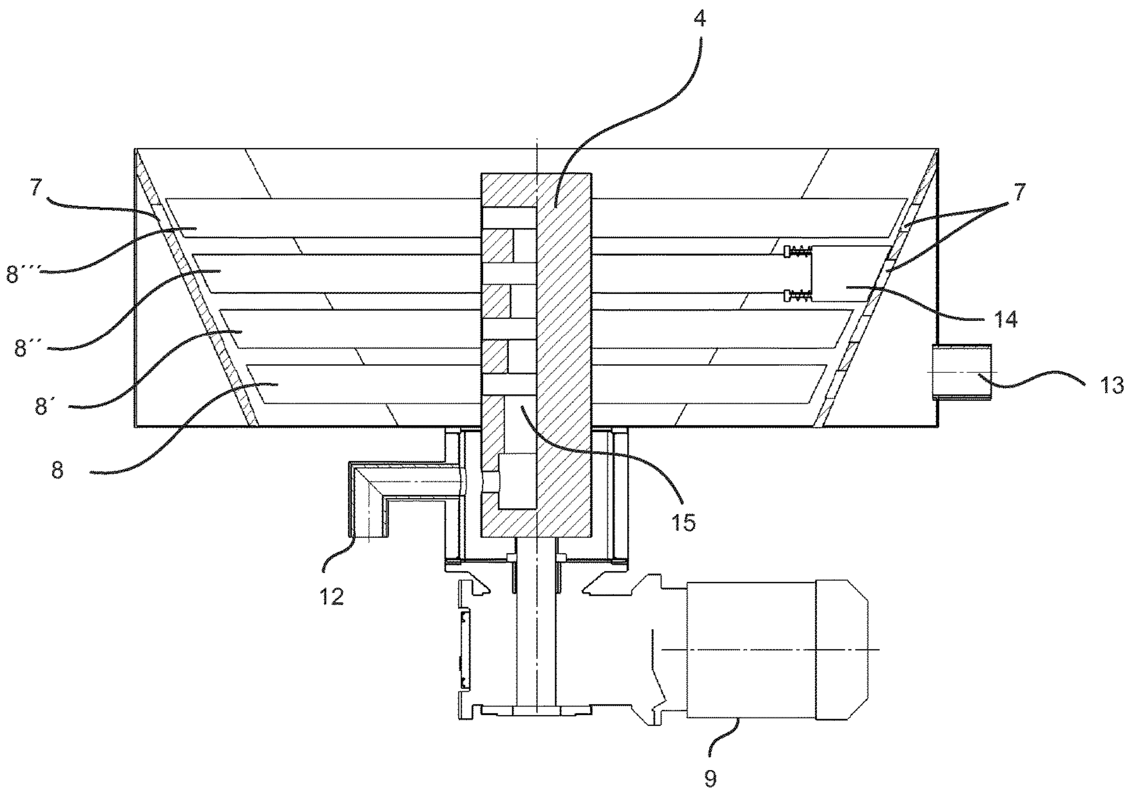
Figure 3:
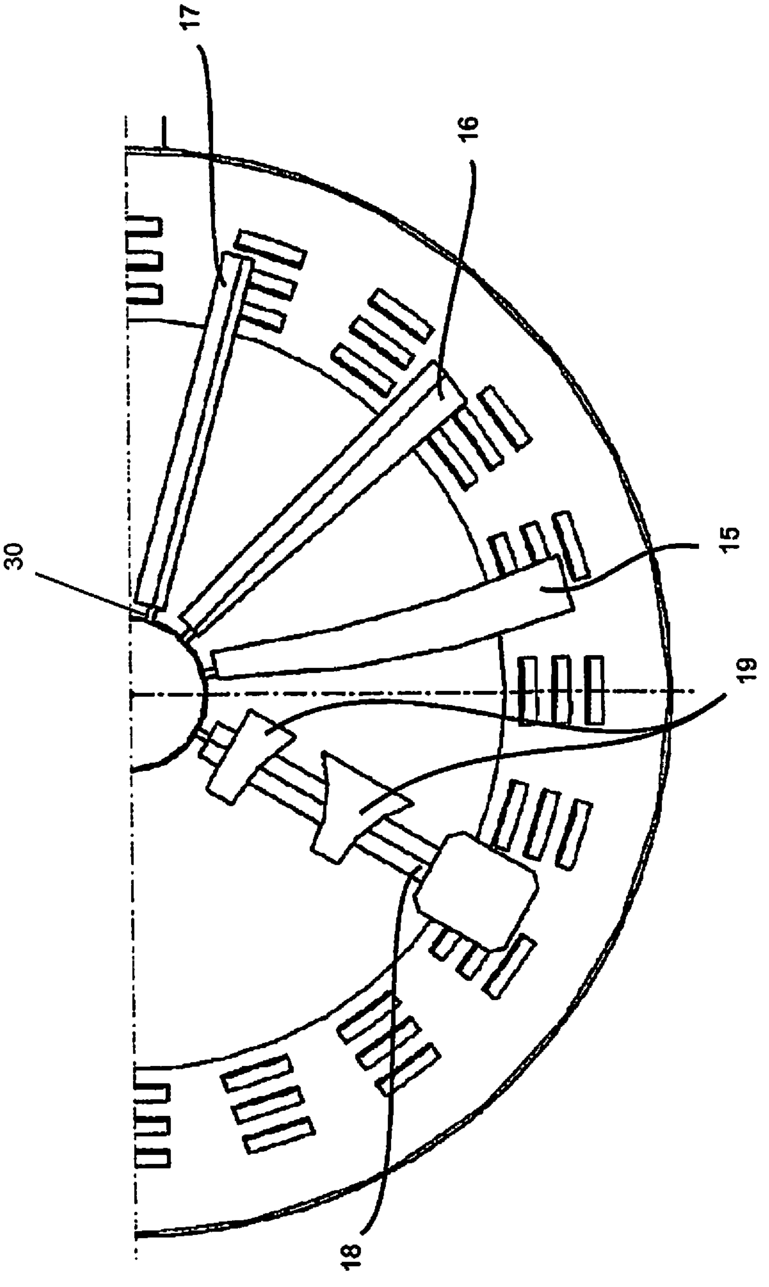
Figure 4:
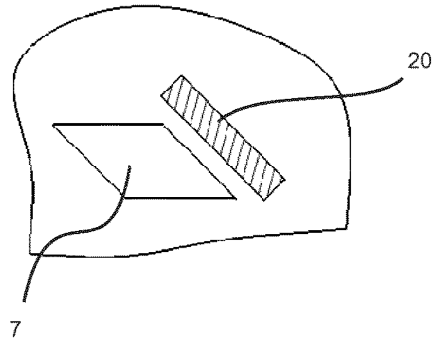
Figure 5:
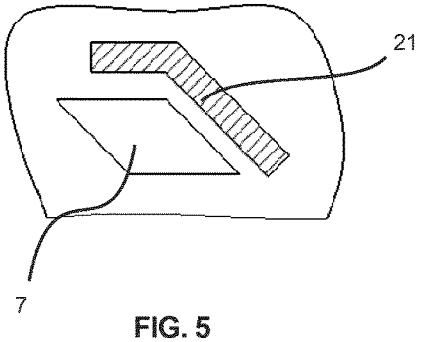
FIG. 5 shows a cross-sectional view of a second embodiment of a mixer blade 21. Here the mixer blade comprises an inclined surface and a surface which is angled relative thereto and which extends substantially horizontally.
Figure 6:
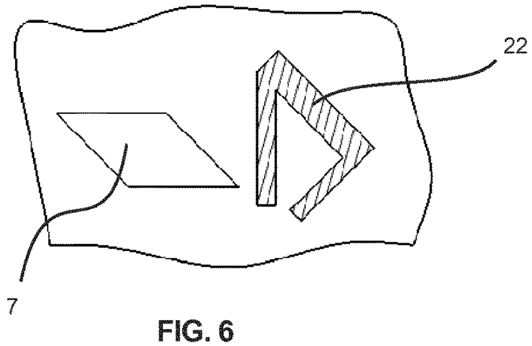
FIG. 6 shows a cross-section through a third embodiment of a mixer blade 2. In this case also there is an inclined surface which is adjoined in one direction by a substantially vertically extending portion and in the other direction by an oppositely inclined portion.
Figure 7:
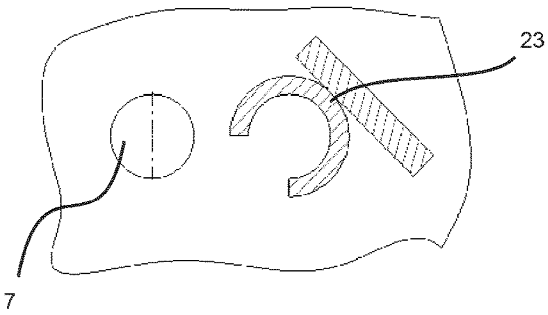

FIG. 7 shows a cross-section through a further embodiment of a mixer blade 23. The mixer blade 23 again has an inclined surface. Here it is mounted to a substantially tubular element, through which cooling air can also be introduced into the mixing container.

Figure 8:
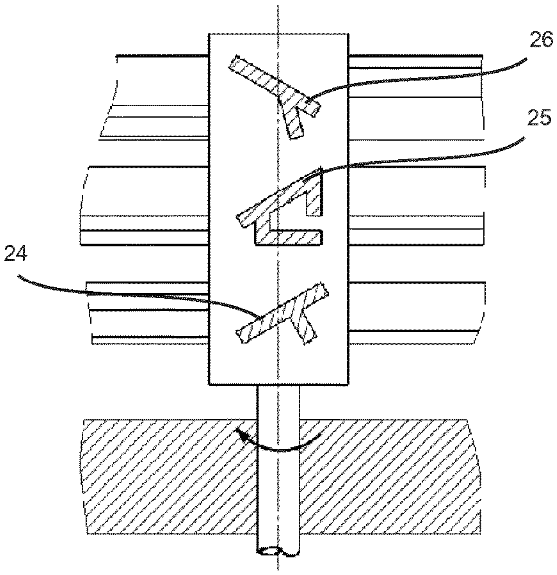

FIG. 8 shows by way of example an embodiment in which different mixer blades 24 to 26 are mounted to the drive shaft in three different planes. The mixer blade arranged in the lowermost plane has a downwardly inclined blade surface and a portion extending substantially perpendicularly thereto. In the central plane a mixer blade 25 is used, involving a cross-section forming a kind of cavity, through which cooling air can be transported from the drive shaft radially outwardly. Used in the uppermost plane is a mixer blade 26 which is inclined upwardly to prevent the material being mixed from being swirled up excessively. It is self-evident that further geometries are possible for the design configuration of the mixer blade.

LIST OF REFERENCES

1 apparatus
2 mixer blade
3 housing
4 drive shaft
5, 5' inlet, outlet
6 conveyor belt
7 air inlet openings
8, 8', 8" mixer blades

9 drive motors
10 drive motor
11 solids separator
12 feed
13 air feed
14 extension portion
15-18 mixer blades
19 attachments
20-26 mixer blades

The invention claimed is:

1. Apparatus for treating and cooling foundry moulding sand, comprising a mixing container and a mixing tool rotatable about a drive shaft, wherein there is provided an air feed for the feed of air into the container interior, characterised in that the mixing tool has at least two mixing vanes spaced from each other in the vertical direction and at least one mixing vane has a mixer blade with a surface which is inclined relative to the horizontal wherein the mixing tool has at least two vertically spaced mixing vanes with mixer blades, wherein a mixer blade has a surface inclined upwardly in the direction of rotation of the mixing tool, wherein the mixer blades extend substantially to a container wall, characterized in that the air feed has openings in the container wall, through which air can be blown into the container interior, wherein the openings are arranged at the same vertical height as the mixer blades which extend substantially to the container wall.

2. Apparatus according to claim 1 characterised in that the surface of the mixer blade is inclined downwardly in the direction of rotation of the mixing tool.

3. Apparatus according to claim 1 characterised in that the spacing between mixer blade and container wall is less than 100 mm.

4. Apparatus according to claim 1 characterised in that there is provided a drive for rotating the mixing tool, wherein the drive is so designed that the mixer blade has a peripheral speed at its radially outer end of between 2 and 75 m/s.

5. Apparatus according to claim 1 characterised in that the container wall is inclined so that the container cross-section becomes larger in an upward direction from the container bottom.

6. Apparatus according to claim 5 characterised in that each mixing vane has a mixer blade, wherein the spacing between mixer blade and container wall is approximately the same for all mixer blades.

7. Apparatus according to claim 1 characterised in that the mixer blade is arranged substantially at the container bottom.

8. Apparatus according to claim 1 characterised in that the container has at least two-mixing portions, wherein provided in each mixing portion is a respective mixing tool rotatable about a drive shaft.

9. Apparatus according to claim 8 characterised in that there is provided a drive device with which each mixing tool can be driven with a peripheral speed which is adjustable independently of each other at the mixing vanes.

10. Apparatus according to claim 8 characterised in that each mixing tool has a mixer blade arranged substantially at the container bottom, wherein the two mixing tools are spaced from each other so far that the two mixer blades arranged at the container bottom do not touch each other in any position of the mixing tools.

11. Apparatus according to claim 8 characterised in that each mixing tool has a mixing vane with a mixer blade which is not arranged at the container bottom, wherein the mixer blades which are not arranged at the container bottom are arranged at different axial heights.

12. Apparatus according to claim 8 characterised in that at least one mixing vane of the mixing tool describes a circular path which in a projection on to a parallel plane intersects with a projection of a circular path described by at least one mixing vane of the other mixing tool on to the same parallel plane.

13. Apparatus according to claim 1 characterised in that the air feed is effected by way of the mixing tool which has a hollow shaft.

14. Apparatus according to claim 1 characterised in that the mixer blade is of a width which enlarges in the radial direction.

15. Apparatus according to claim 1 characterised in that the mixer blade is in the form of an angled profile, wherein the inner angle is opposite to the direction of rotation of the mixer blade.

16. Apparatus according to claim 1 characterised in that the mixer blade has air outlet openings on its side oriented in opposite relationship to the direction of rotation.

17. Apparatus according to claim 1 characterised in that a solids separator is arranged above the mixing tool, wherein the solids separator is so designed that by means of a rotor it produces a rotational flow.

18. Apparatus according to claim 1 characterised in that the mixer blade extends substantially to the container wall, wherein there is provided an attachment which is associated with the mixer blade and which projects in the direction of the container wall beyond the mixer blade and contacts the container wall.

19. Apparatus according to claim 8 wherein each mixing tool has at least two mixing vanes spaced from each other in the vertical direction.

* * * * *